United States Patent [19]

Nedenskov et al.

[11] 4,048,198

[45] Sept. 13, 1977

[54] CERTAIN 8-(2-TETRAHYDROFURYL)OCTANOIC ACID COMPOUNDS WITH PROSTAGLANDIN LIKE BIOLOGICAL EFFECTS

[75] Inventors: Poul Nedenskov, Birkerod; Karol Alster, Farum, both of Denmark

[73] Assignee: Aktieselskabet Grindstedvaerket, Arhus, Denmark

[21] Appl. No.: 686,987

[22] Filed: May 17, 1976

Related U.S. Application Data

[63] Continuation-in-part of Ser. No. 480,722, June 19, 1974, abandoned.

[30] Foreign Application Priority Data

June 20, 1973   United Kingdom ............... 29241/73

[51] Int. Cl.$^2$ ........................................... C07D 307/16
[52] U.S. Cl. .............................. 260/347.4; 260/347.3; 424/285

[58] Field of Search ................ 260/347.3, 347.5, 347.4

[56] References Cited

PUBLICATIONS

Korskaya et al., Ch. Ab. (1974), vol. 80, 95628.

*Primary Examiner*—Henry R. Jiles
*Assistant Examiner*—Bernard Dentz
*Attorney, Agent, or Firm*—Lawrence Rosen; E. Janet Berry

[57] ABSTRACT

This invention relates to therapeutically active 2,5-tetrahydrofurane derivatives, wherein the substituent in the 2-position is a group ROOC—$(CH_2)_7$, in which R is hydrogen or lower alkyl, the 5-substituent being an alkyl or alkenyl group of 8 to 12 carbon atoms, which may be substituted with an oxygen atom, a hydroxy group or a lower alkyl group at the third carbon atom, counted from the furane ring, and to the production thereof.

8 Claims, No Drawings

CERTAIN 8-(2-TETRAHYDROFURYL)OCTANOIC ACID COMPOUNDS WITH PROSTAGLANDIN LIKE BIOLOGICAL EFFECTS

This application is a continuation-in-part of the patent application Ser. No. 480,722, filed June 19, 1974, now abandoned.

The present invention relates to novel 2,5-tetrahydrofurane derivatives represented by the formula

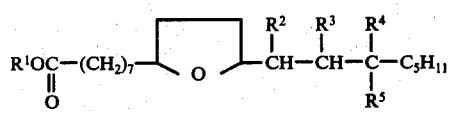

wherein $R^1$ represents hydrogen or a lower alkyl group, each of $R^2$ and $R^3$ represents hydrogen, or $R^2$ and $R^3$ together represents a further bond between the two carbon atoms; one of $R^4$ and $R^5$ represents hydrogen or a lower alkyl group, and the other a hydroxy group, or $R^4$ and $R^5$ together represent an oxygen atom.

When the present compounds have asymmetric centers, the invention comprises racemates as well as the individual isomers.

As used in this specification, a lower alkyl group should be understood as being an alkyl group having 1 to 4 carbon atoms.

The compounds of the invention have useful biological properties combined with low toxicity. Thus, they have a controlling effect upon the activity of the symphathetic nervous system, giving new possibilities for the treatment of hypertension.

More specifically, the novel compounds are very potent and have biological effects similar to those of prostaglandins of the E and F series. They can, therefore, be used in place of or in combination with less than the usual amounts of these prostaglandins and other known compounds with similar biological activities to alleviate or prevent conditions of, for example, abnormal uterine motility and of platelet aggregation.

Preferred compounds of the invention are those in which $R^1$, $R^2$, and $R^3$ in the above formula represent hydrogen, and $R^4$ is methyl and $R^5$ is hydroxy, or $R^4$ and $R^5$ together is oxygen, and those in which $R^1$ and $R^4$ are hydrogen and $R^5$ is hydroxy.

The novel compounds are very potent inhibitors of the spontaneous motility of isolated strips of the human myometrium. Accordingly, these compounds will be useful in conditions when this motility is abnormally high, e.g. in dysmenorrhoea, threatening abortion and premature labor. In addition, they can be used for treatment of infertility when this condition is caused by too low a content of prostaglandins in the seminal plasma. For the above purposes, the compounds are to be used, orally or by way of injection whichever is most suitable in the individual case, in a dose range of from 0.5 to 10 mg per kg body weight, depending of the age and weight of the patient, the indication, and the route of administration.

The novel compounds are also active as inhibitors of the aggregation of platelets when the aggregation is tested according to the method of Born (Nature 124 (1962) 927). Accordingly, these compounds can be used to alleviate or prevent thrombosis and emboli following various forms of trauma, e.g. accidents, fractures, operations. For this purpose the compounds are to be administered in a dose range of 0.1 to 100 mg/kg body weight, depending of the age and weight of the patient and the route of administration.

In all cases, where the present compounds exist in isomeric configurations, the above dose ranges relate to the racemate mixtures.

The following schemes of reaction illustrate the production of the compounds of the invention:

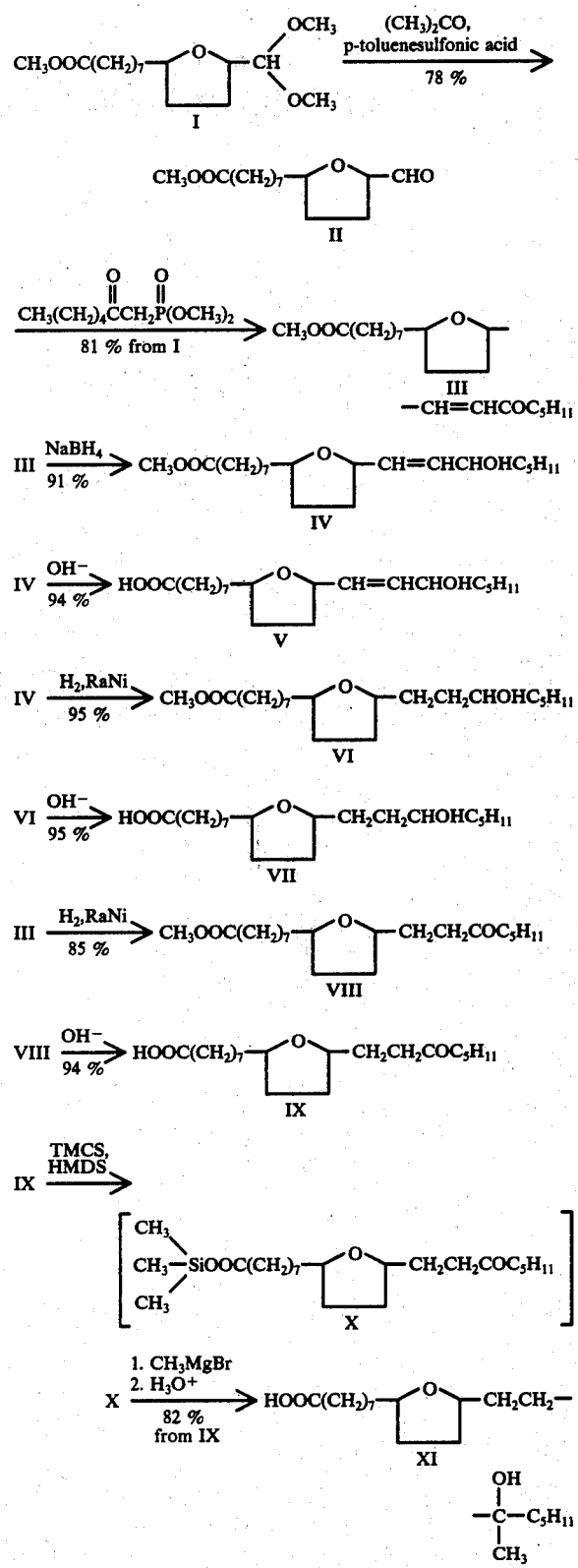

-continued

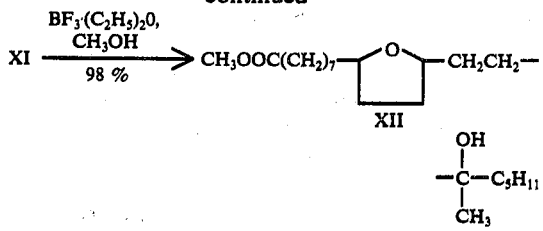

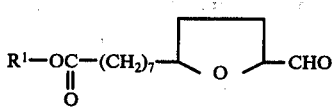

The starting materials for the production of the compounds of the invention are tetrahydrofurane derivatives of the formula:

wherein R¹ is as hereinbefore defined.

The said starting materials are new compounds, which can be produced e.g. from the 8-(5-dimethoxymethyl-tetrahydro-2-furyl)-octanoic acid methyl ester known from U.S. patent application Ser. No. 341,627, filed Mar. 15, 1973 (U.S. Pat. No. 4,009,187), which claims the priority of the British patent specification No. 12940/72.

The starting aldehydes are condensed with the appropriate alkane-2-one, e.g. 2-heptanone, possibly in the form of its dimethylphosphoric acid ester, resulting in the formation of a 3-oxo-1-alkenyl group at the 5-position of the tetrahydrofurane ring, and optionally hydrogenating the double bond, reducing the keto group to a hydroxy group, or transforming the keto group into hydroxyl and a lower alkyl group by a Grignard reaction.

When R¹ represents hydrogen in the resulting compound, the carboxyl group may subsequently be esterified to yield esters of the invention, or, if the resulting compound is an ester, it may be saponified to yield the corresponding acid.

The introduction of the side chain in 5-position is preferably carried out at room temperature in solution in an alkanol, e.g. methanol or ethanol.

Suitable catalysts for the hydrogenation are Raney nickel, Raney copper, and noble metal catalysts, e.g. palladium.

The following examples are illustratives of the production of the present compounds, the various compounds being identified by the numbering in the above schemes of reaction.

EXAMPLE 1

A. 8-(5-Formyl-tetrahydro-2-furyl)-octanoic acid methyl ester (II)

8-(5-Dimethoxymethyl-tetrahydro-2-furyl)-octanoic acid methyl ester (I) (1.51 g, 0.00500 mole), p-toluenesulfonic acid (30 mg), and acetone (50 ml) were stirred and heated for about 6 hours in such a way that every 30 minutes about 30 ml of the acetone were distilled off, and a similar new portion of acetone was added to the reaction mixture. The reaction was followed by thin layer chromatography (tlc). After cooling, sodium bicarbonate (0.1 g) was added, and the suspension was stirred for 1 hour. After filtration, the solvent was removed by heating on a water bath (60° C, 10 mmHg), and the residual yellow oil (1.45 g) was purified by distillation, giving 1.00 g (78%) of II as a colourless oil, $b_{0.05}$ 119°–122° C, $n_D^{25}$ 1.4603.

Calculated for $C_{14}H_{24}O_4$ (256.3): C, 65.6; H, 9.4. Found: C, 65.4; H, 9.6.

B. 8-[5-(3-Oxo-1-octenyl)-tetrahydro-2-furyl]-octanoic acid methyl ester (III)

50% sodium hydride in mineral oil (1.11 g, 0.0230 mole) was suspended in 1,2-dimethoxyethane (115 ml). At 15° C and under vigorous stirring (2-oxoheptyl)-phosphoric acid dimethyl ester (5.11 g, 0.0230 mole) in dimethoxyethane (23 ml) was added dropwise over a period of 15 minutes. The reaction mixture containing a white voluminous precipitate was stirred for 1 hour at room temperature. A solution of crude II (7.20 g), prepared from I (7.55 g, 0.0250 mole), in 1,2-dimethoxyethane (46 ml) was added dropwise over a period of 15 minutes to the stirred reaction mixture, maintained below 25° C. The resulting turbid, yellow solution was stirred at room temperature for 2 hours. The solvent was distilled off from a water bath (40° C, 10 mm Hg). The oily residue was dissolved in ether (230 ml), washed with cold 10% aqueous sodium chloride (60 + 60 + 60 ml) and cold water (60 + 60 ml), and dried over sodium sulfate. After filtration, the solvent was removed from a water bath (60° C, 10 mm Hg). The residual light tea-coloured oil (9.60 g) was distilled under nitrogen to give 7.15 g (81%) of III as a light yellowish oil, $b_{0.05}$ 160°–190° C, $n_D^{25}$ 1.4712.

For analysis 1.00 g of III ($b_{0.05}$ 160°–190° C) was purified by chromatography on silica gel (ether-ligroine (b. <50° C) 1:1 as eluent) to give 0.80 g of a light yellow oil. Distillation (185°–190° C, 0.03 mm Hg) yielded 0.62 g of III as a light yellowish oil, $n_D^{25}$ 1.4756.

Calculated for $C_{21}H_{36}O_4$ (352.5): C, 71.6; H, 10.3. Found: C, 71.8; H, 10.2.

EXAMPLE 2

8-[5-(3-Hydroxy-1-octenyl)-tetrahydro-2-furyl]-octanoic acid methyl ester (IV)

III (3.17 g, 0.00900 mole) was dissolved in methanol (75 ml) and sodium tetrahydroborate (1.7 g, 0.045 mole) was added at 0° C with stirring. The stirring was continued for 1 hour. During this time the temperature was slowly raised to room temperature. The colourless solution was poured into ice-water (250 ml) and extracted with ether (100 + 50 + 50 ml). The combined ethereal extracts were washed with water (50 + 25 + 25 ml), dried over magnesium sulfate, and evaporated from a water bath (50° C, 10 mm Hg). The obtained light yellowish oil (3.38 g) was distilled under reduced pressure to give 2.90 g (91%) of IV as a colourless oil, $b_{0.05}$ 175°–188° C, $n_D^{25}$ 1.4699.

For analysis 0.72 g of IV ($b_{0.05}$ 175°–188° C) was purified by chromatography on silica gel (ether-ligroine (b. < 50° C) 1:1 as eluent) to give 0.65 g of a colourless oil. Distillation (185°–190° C, 0.05 mm Hg) yielded 0.55 g of IV as a colourless oil, $n_D^{25}$ 1.4711.

Calculated for $C_{21}H_{38}O_4$ (354.5): C, 71.1; H, 10.8. Found: C, 71.3; H, 10.8.

EXAMPLE 3

8-[5-(3-Hydroxy-1-octenyl)-tetrahydro-2-furyl]-octanoic acid (V)

IV (1.77 g, 0.00500 mole), methanol 20 ml), and 20% aqueous potassium carbonate (10 ml) were stirred and heated under reflux for 90 minutes. The methanol was removed from a water bath (60° C, 100 mm Hg). The residue was diluted with water (25 ml) and washed with ether (25 ml). The resulting clear solution was acidified to pH 5–6 with acetic acid. The resulting emulsion was extracted with ether (25 + 25 ml). The combined ethereal extracts were dried over sodium sulfate and evaporated from a water bath (60° C, 1 mm Hg) to give 1.60 g (94%) of V as a colourless oil, $n_D^{25}$ 1.4778.

For analysis, 1.60 g of V ($n_D^{25}$ 1.4778) was purified by chromatography on silica gel (ether-ligroine (b. <50° C) 2:1 as eluent) to give 1.30 g of a colourless oil. Distillation (190°–195° C, 0.04 mm Hg) yielded 1.04 g of V as a colourless oil, $n_D^{25}$ 1.4790.

Calculated for $C_{20}H_{36}O_4$ (340.5): C, 70.5; H, 10.7. Found: C, 70.3; H, 10.7.

EXAMPLE 4

8-[5-(3-Hydroxyoctyl)-tetrahydro-2-furyl]-octanoic acid methyl ester (VI)

IV (1.77 g, 0.00500 mole), methanol (50 ml), and Raney nickel (1 g) were shaken under hydrogen at a pressure of 70 atmospheres for 24 hours at room temperature. After filtration, the solvent was removed from a water bath (60° C, 10 mm Hg). Ether (50 ml) was added to the residue, and the turbid, colourless solution was filtered. The ethereal solution was evaporated to dryness from a water bath (60° C, 10 mm Hg). The residual clear, colourless oil (1.90 g) was distilled under reduced pressure to give 1.69 g (95%) of VI as a colourless oil, $b_{0.05}$ 160°–172° C, $n_D^{25}$ 1.4625.

For analysis, 1.50 g of VI ($b_{0.05}$ 160°–172° C) was purified by chromatography on silica gel (ether-ligroine (b. <50° C) 1:1 as eluent) to give 1.20 g of a colourless oil. Distillation under reduced pressure gave 1.05 g of VI as a colourless oil, $b_{0.1}$ 175°–176° C, $n_D^{25}$ 1.4630.

Calculated for $C_{21}H_{40}O_4$ (356.5): C, 70.7; H, 11.3. Found: C, 70.8; H, 11.3.

EXAMPLE 5

8-[5-(3-Hydroxyoctyl)-tetrahydro-2-furyl]-octanoic acid (VII)

VI (1.78 g, 0.00500 mole), methanol (20 ml), and 20% aqueous potassium carbonate (10 ml) were stirred and heated under reflux for 90 minutes. The methanol was removed from a water bath (60° C, 100 mm Hg). The residue was diluted with water (25 ml) and washed with ether (25 ml). The resulting clear solution was acidified to pH 5–6 with acetic acid. An emulsion was formed, which was extracted with ether (25 + 25 ml). The combined ethereal extracts were dried over sodium sulfate and evaporated from a water bath (60° C, 1 mm Hg) to give 1.62 g (95%) of VII as a light yellowish oil, $n_D^{25}$ 1.4682.

For analysis, 1.62 g of VII ($n_D^{25}$ 1.4682) was purified by chromatography on silica gel (ether-ligroine (b. <50° C) 2:1 as eluent) to give 1.20 g of a light yellowish oil. Distillation (180°–190° C, 0.03 mm Hg) yielded 0.85 g of VII as a light yellowish oil, which solidified on standing. M.p. 32°–33° C, $n_D^{25}$ 1.4713.

Calculated for $C_{20}H_{38}O_4$ (342.5): C, 70.1; H, 11.2. Found: C, 69.9; H, 11.1.

EXAMPLE 6

8-[5-(3-Oxooctyl)-tetrahydro-2-furyl]-octanoic acid methyl ester (VIII)

III (3.52 g, 0.0100 mole) methanol (50 ml), and Raney nickel (0.5 g) were stirred under hydrogen at a pressure of 1 atmosphere, until absorption stopped. After filtration, the solvent was removed from a water bath (60° C, 10 mm Hg). The residual light yellowish oil (3.60 g) was distilled under reduced pressure to give 3.01 g (85%) of VIII as a light yellowish oil, $b_{0.03}$ 165°–176° C, $n_D^{25}$ 1.4608.

For analysis, 3.01 g of VIII ($b_{0.03}$ 165°–176° C) was purified by chromatography on silica gel (ether-ligroine (b. <50° C) 1:2 as eluent) to give 2.06 g of a colourless oil. Distillation under reduced pressure gave 1.95 g of VIII as a colourless oil, $b_{0.03}$ 172°–174° C, $n_D^{25}$ 1.4600.

Calculated for $C_{21}H_{38}O_4$ (354.5): C, 71.1; H, 10.8. Found: C, 71.0; H, 10.9.

EXAMPLE 7

8-[5-(3-Oxooctyl)-tetrahydro-2-furyl]-octanoic acid (IX)

VIII (1.77 g, 0.00500 mole), methanol (20 ml), and 20% aqueous potassium carbonate (10 ml) were stirred and heated under reflux for 2.5 hours. The methanol was removed fron a water bath (60° C, 100 mm Hg). The residue was diluted with water (25 ml) and washed with ether (25 ml). The resulting clear solution was acidified to pH 5–6 with acetic acid. The emulsion being formed was extracted with ether (25 + 25 ml). The combined ethereal extracts were dried over sodium sulfate and evaporated from a water bath (60° C, 1 mm Hg). The yellowish, oily residue of IX (1.60 g, 94%) solidified by standing. M.p. 26°–28° C, $n_D^{25}$ 1.4673.

For analysis, 1.60 g of IX (m.p. 26°–28° C) was purified by chromatography on silica gel (ether-ligroine (b. <50° C) 1:1 as eluent) to give 1.30 g of a light yellowish oil. Distillation under reduced pressure yielded 0.88 g of IX as a light yellowish oil, which solidified by standing, $b_{0.05}$ 200°–202° C, m.p. 31°–32° C, $n_D^{25}$ 1.4686.

Calculated for $C_{20}H_{36}O_4$ (340.5): C, 70.5; H, 10.7. Found: C, 70.5; H, 10.7.

EXAMPLE 8

8-[5-(3-Hydroxy-3-methyloctyl)-tetrahydro-2-furyl]-octanoic acid (XI)

IX (6.30 g, 0.0185 mole), hexamethyldisilazane (HMDS) (12 ml), trimethylchlorosilane (TMCS) (6 ml), and pyridine (40 ml) were mixed and kept overnight at room temperature. The resulting white suspension was evaporated to dryness (50° C, 10 mm Hg). Ether (100 ml) was added, and the suspension was filtered. The resulting clear, yellow solution of X was cooled to 0° C, and methylmagnesium bromide in ether (3.8N, 8.0 ml, 0.030 mole) was added dropwise during 20 minutes. After stirring for 2 hours at room temperature, the white suspension being formed was poured into a mixture of cold hydrochloric acid (0.25N, 140 ml) and ether (50 ml). The ethereal phase was separated, and the aqueous layer was extracted with ether (50 + 25 ml). The combined ethereal extracts were washed with water 50 ml) and dried over sodium sulfate. The solvent was removed from a water bath (60° C, 10 mm Hg), and the residual light yellowish oil (7.40 g) was distilled under reduced pressure to give 5.40 g (82%) of XI as a light yellowish oil, $b_{0.08}$ 203°–210° C, $n_D^{25}$ 1.4710.

For analysis, 1.50 g of XI ($b_{0.08}$ 203°–210° C) was purified by chromatography on silica gel (ether-ligroine (b. <50° C) 1:1 as eluent) to give 1.10 g of a light yellowish oil. Distillation (190°–200° C, 0.05 mm Hg) yielded 1.00 g of XI as a light yellowish oil, $n_D^{25}$ 1.4725.

Calculated for $C_{21}H_{40}O_4$ (356.5): C, 70.7; H, 11.3. Found: C, 70.5; H, 11.2.

EXAMPLE 9

8-[5-(3-Hydroxy-3-methyloctyl)-tetrahydro-2-furyl]-octanoic acid methyl ester (XII)

XI (1.78 g, 0.00500 mole), methanol (25 ml), and ethyl ether-borontrifluoride complex (0.1 ml) were stirred and heated under reflux for 1 hour. After cooling, the reaction mixture was poured into ice-water (200 ml) and extracted with ether (50 + 50 + 25 ml). The combined ethereal extracts were washed with cold 2% aqueous sodium hydrogen carbonate (50 ml) and water (50 ml). The ethereal solution was dried over sodium sulfate and evaporated to dryness from a water bath (60° C, 10 mm Hg). The residual yellowish oil (1.95 g) was distilled under reduced pressure to give 1.82 g (98%) of XII as a colourless oil, $b_{0.03}$ 160°–170° C, $n_D^{25}$ 1.4625.

For analysis, 1.80 g of XII ($b_{0.03}$ 160°–170° C) was purified by chromatography on silica gel (ether-ligroine (b. <50° C) 1:1 as eluent) to give 1.00 g of colourless oil. Distillation (150°–160° C, 0.05 mm Hg) yielded 0.75 g of XII as a colourless oil, $n_D^{25}$ 1.4640.

Calculated for $C_{22}H_{42}O_4$ (370.6): C, 71.3; H, 11.4. Found: C, 71.1; H, 11.4.

We claim:

1. A tetrahydrofuran derivative of the formula

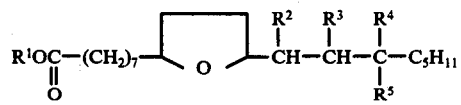

wherein $R^1$ represents hydrogen or a lower alkyl group, each of $R^2$ and $R^3$ represents hydrogen, or $R^2$ and $R^3$ together represents a further bond between the two carbon atoms, one of $R^4$ and $R^5$ represents hydrogen or a lower alkyl group and the other a hydroxy group, or $R^4$ and $R^5$ together represents an oxygen atom.

2. A compound of claim 1, in which $R^1$ is hydrogen, and esters thereof with alkanols of 1–4 carbon atoms.

3. A compound of claim 1, in which $R^1$ is methyl, $R^2$ and $R^3$ together is a further bond between the carbon atoms, and $R^4$ and $R^5$ together is oxygen.

4. A compound of claim 1, in which $R^1$ is methyl, $R^2$ and $R^3$ together is a further bond between the carbon atoms, $R^4$ is hydrogen, and $R^5$ is hydroxy.

5. A compound of claim 1, in which $R^1$ is methyl, $R^2$ and $R^3$ are hydrogen, and $R^4$ and $R^5$ together is oxygen.

6. A compound of claim 1, in which $R^1$ is hydrogen, $R^2$ and $R^3$ together is a further bond between the carbon atoms, and $R^4$ and $R^5$ together is oxygen, and the esters thereof with $C_1$–$C_4$ alkanols.

7. A compound of claim 1, in which $R^1$, $R^2$, $R^3$, and $R^4$ are hydrogen, and $R^5$ is hydroxy, and the esters thereof with $C_1$–$C_4$ alkanols.

8. A compound of claim 1, in which $R^1$, $R^2$, and $R^3$ are hydrogen, $R^4$ is methyl, and $R^5$ is hydroxy, and esters thereof with $C_1$–$C_4$ alkanols.

* * * * *